(12) United States Patent
Lundell et al.

(10) Patent No.: US 6,735,802 B1
(45) Date of Patent: May 18, 2004

(54) BRUSHHEAD REPLACEMENT INDICATOR SYSTEM FOR POWER TOOTHBRUSHES

(75) Inventors: William G. Lundell, Issaquah, WA (US); Clifford Jue, Santa Cruz, CA (US); Annetta M. Papadopoulos, Palo Alto, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/567,829

(22) Filed: May 9, 2000

(51) Int. Cl.[7] .............................................. A61C 17/22
(52) U.S. Cl. .................... 15/22.1; 15/105; 15/167.1; 433/216
(58) Field of Search ................ 15/22.1, 105, 167.1; 433/216; 368/109

(56) References Cited

U.S. PATENT DOCUMENTS

| | | | | |
|---|---|---|---|---|
| 5,485,646 A | * | 1/1996 | Merritt ........................ | 15/105 |
| 5,546,624 A | * | 8/1996 | Bock .......................... | 310/318 |
| 5,561,881 A | * | 10/1996 | Klinger et al. ................ | 15/22.1 |
| 5,572,762 A | * | 11/1996 | Scheiner ...................... | 15/105 |
| 5,704,087 A | * | 1/1998 | Strub .......................... | 15/22.1 |
| 6,246,153 B1 | * | 6/2001 | Bishop et al. ................ | 15/105 |
| 2002/0088068 A1 | * | 7/2002 | Levy et al. ................... | 15/22.1 |

FOREIGN PATENT DOCUMENTS

DE 19728964 A1 * 1/1999 ........... A61C/17/00

* cited by examiner

Primary Examiner—Robert J. Warden, Sr.
Assistant Examiner—Shay L Balsis
(74) Attorney, Agent, or Firm—Ernestine C. Bartlett

(57) ABSTRACT

A system for determining when the brushhead portion of a power toothbrush should be replaced. The system includes a piezoelectric transducer for detecting oscillations of the brushhead. The piezoelectric transducer produces an output signal which is used to drive a counter which accumulates the total number of such oscillations. When the total number of oscillations reaches a preselected number, which is representative of typical use of the toothbrush for a predetermined amount of time, e.g. six months, a signal is produced which drives an alarm indicator, the action of which is recognizable by the user of the toothbrush.

14 Claims, 1 Drawing Sheet

BRUSHHEAD REPLACEMENT INDICATOR SYSTEM FOR POWER TOOTHBRUSHES

TECHNICAL FIELD

This invention relates generally to the art of power toothbrushes and more specifically concerns a system for indicating when a brushhead portion of a power toothbrush should be replaced.

BACKGROUND OF THE INVENTION

It is generally agreed that toothbrushes are not replaced as frequently as is usually recommended by dentists. This includes the removable brushhead portion of power toothbrushes. Such brushheads can wear out to the point of significant reduction in effectiveness, but may not show any obvious signs of wear, or obvious indication of performance deterioration. Reduced brush effectiveness, of course, is undesirable relative to maintaining good dental health.

There have been various attempts to address the failure to replace brushheads in timely (and healthy) fashion by the use of dye impregnated bristles or a colored bristle sheath, which are both capable of showing signs of wear. The indication of wear by such structural means, however, is not precise and hence may not provide definitive guidance to the user as to when the brushhead should be replaced.

Hence, there is a need for a system of precisely and clearly indicating to the user when a brushhead should be replaced so as to maintain high level of brushing performance and effectiveness.

SUMMARY OF THE INVENTION

Accordingly, the present invention is a system for determining automatically when a brushhead portion of a power toothbrush should be replaced and for providing an indication thereof to the user, comprising: A system carried within the toothbrush for detecting and accumulating the number of occurrences of a characteristic directly related to actual use of the toothbrush; means for determining when the number of said occurrences of said characteristic of toothbrush use reaches a preselected number, said preselected number correlating to sufficient use of the brushhead that the brushhead should be replaced; and an indicator, such as a visual or audible alarm, for communicating to the user that the brushhead should be replaced.

BEST MODE FOR CARRYING OUT THE INVENTION

Figure 1:
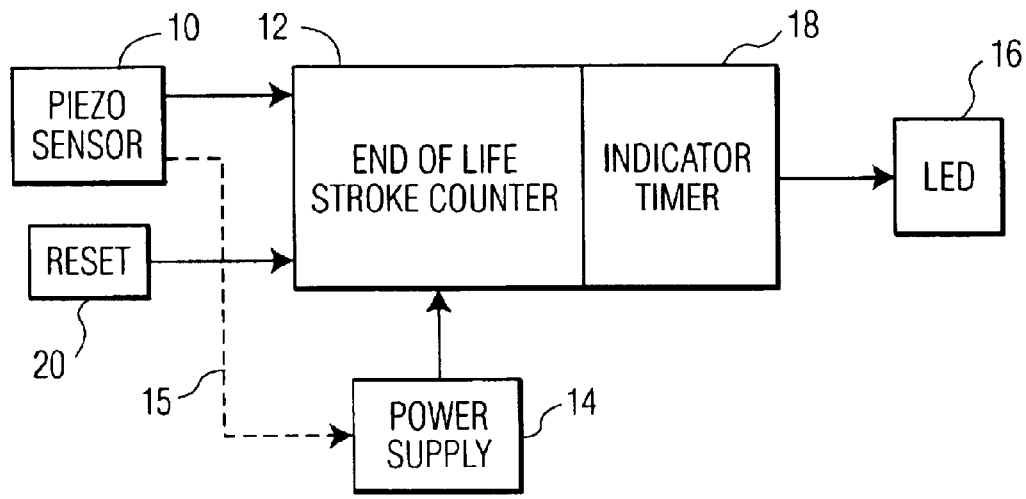
FIG. 1 is a block diagram of one embodiment of the system of the present invention.

FIG. 1 shows a block diagram of the brushhead replacement indicator system of the present invention. The present invention provides a replacement indication based on the actual use of the toothbrush, specifically the number of oscillations/vibrations of the brushhead. The oscillations are counted and accumulated for successive uses of the toothbrush. When the number of oscillations reaches a preselected amount, referred to herein as an end-of-life number, an alarm is provided to the user. The end-of-life number and hence the replacement notification is based on a presumed use of the toothbrush twice a day for two minutes each brushing time for six months.

In the embodiment shown, the system of the present invention is used in a power toothbrush that oscillates at approximately 260 Hz. Such a toothbrush is shown in U.S. Pat. No. 5,189,751, which is owned by the assignee of the present invention. It should be understood, however, that the present invention can be used with other power toothbrushes with different frequencies of oscillation/vibration.

In each case, however, the preselected total number of oscillations (the end-of-life number) at which the replacement alarm is provided must take into account the oscillating frequency of the brushhead. In the specific case of a frequency of 260 Hz, the number of oscillations for the above-discussed use is 11,232,000. The six month period of use is generally considered to be the time during which the brushhead provides effective results. Beyond that point, accumulated wear results in decreased performance/effectiveness. It should be understood, however, that the six month period is not absolute (it could differ) and hence the end-of-life number can be modified, depending upon the actual number of oscillations found to result in unacceptably reduced effectiveness for a particular brushhead with a typical manner of use.

Referring to FIG. 1, the actual number of individual oscillations or vibrations (the terms oscillation/vibration refers to one complete back and forth movement of the brushhead) is detected by a piezoelectric sensor 10. The piezoelectric sensor 10 is arranged relative to the brushhead or mounting arm so as to sense the mechanical vibration of the brushhead. It produces an electrical signal output corresponding to the vibration. Other means of detecting the oscillations of the brushhead include other vibration sensors, switches or even optical devices.

The output of piezoelectric sensor 10 is converted into a square wave which is applied to what is referred to as a stroke counter circuit 12. The piezoelectric sensor 10 also will generate enough power to run the counter circuit 12 during actual brushing/counting. This is a significant feature of the present arrangement. This is indicated by the dotted line 15 which connects the piezoelectric sensor 10 and power supply 14. Power supply 14, which in the embodiment shown is a three volt battery, maintains the count in memory in counter 12 between successive brushings. There is very little drain on the battery during the counting of the oscillations because of the low current requirements of the stroke counter memory and because the piezoelectric sensor 10 provides power to the counter.

In the embodiment shown, the piezoelectric sensor also has some control over the action of LED 16, which provides a visual alarm to the user when counter 12 reaches the end-of-life number of oscillations. The use of the piezoelectric sensor relative to LED 16 is discussed in more detail below. In the embodiment of FIG. 1, while the alarm provided to the user is indicated to be visual, provided by a LED, it should be understood that the alarm could be provided by other visual, audible or sensory devices. Counter 12 can be reset by a reset circuit 20 when a new brushhead is put in place, or following an initial test of the operation of the counter at the factory.

Stroke counter 12 in the embodiment shown counts up to an end-of-life number of brush strokes covering a total estimated usage of six months. This end-of-life number, for a frequency of 260 Hz is 11,232,000 oscillations, as indicated above. This number could be changed depending upon the actual desired use time for the brush and the actual frequency of the brushhead. When the end-of-life number is reached, the counter 12 stops accepting new counts and produces an output signal which triggers an indicator timing circuit 18 which in turn controls the operation of LED 16 at selected times, in combination with piezoelectric sensor element 10.

Timing circuit 18 produces a low duty cycle, control pulse to LED 16. The control pulse energizes the LED once per second during a period of two minutes following each brushing event (after the end-of-life number has been reached).

The power supply 14 with its three volt battery not only maintains the memory of the counter 12 between brushings, it also powers the overall circuit and specifically the LED when the LED is energized. As indicated above, however, piezoelectric element 10 provides power to the counter circuit during brushing action. Also, it is possible to use a storage device and a non-volatile memory to produce a system which is entirely self-powered by the piezoelectric element.

Figure 2:
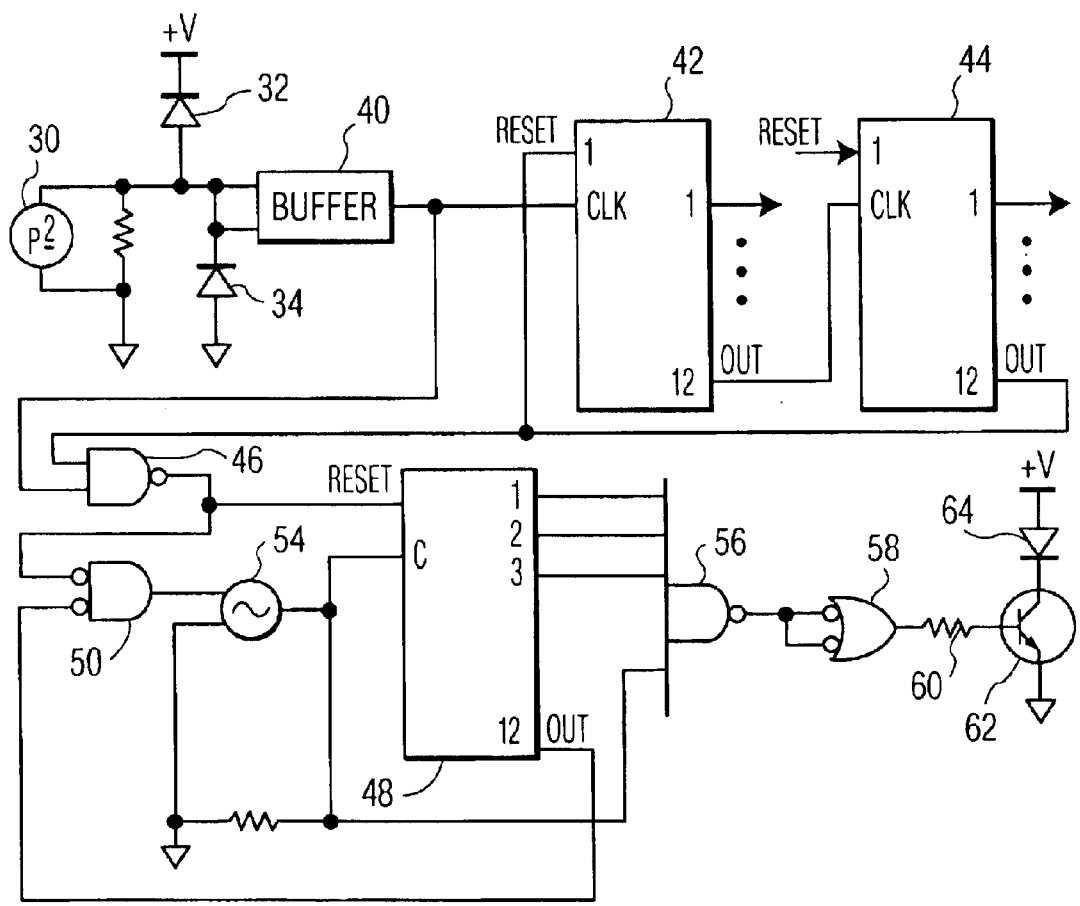
FIG. 2 is a more detailed schematic diagram showing one implementation of the system of FIG. 1.

FIG. 2 shows a schematic diagram of a particular implementation of the circuit of FIG. 1. The piezoelectric element shown at 10 in FIG. 1 is referred to at 30 in FIG. 2. The piezoelectric element is arranged relative to the arm on which the brushhead is mounted such that mechanical action of the brushhead actuates the piezoelectric element, which produces a sine wave signal output, with each output pulse indicating a single back and forth oscillation. The overvoltage of the output signal is rectified and used to power the remainder of the circuit.

Diodes 32 and 34 clip the sine wave output of the piezoelectric transducer to produce a square wave signal and direct the over-voltage part of the output signal, i.e. that part of the signal greater than the square wave required for detection, back to the power supply, which in the embodiment shown comprises a three volt battery (not shown). Alternatively, as indicated above, the power supply could be a storage element, such as a capacitor, in combination with a voltage limiting zener diode. Such an arrangement, with a non-volatile memory, could result in the circuit being self powering.

A buffer element 40 is responsive to diodes 32 and 34 to buffer the output from piezoelectric element 30. The output from buffer 40 is the trigger input to a oscillator/vibration (also referred to as stroke) counter assembly. Counters 42 and 44 combine together to count to the slightly greater than 11 million strokes which is the end-of-life stroke number in the embodiment disclosed. Counter 42 accumulates the first 12 bits, while counter 44 accumulates the second twelve bits, the two counters being cascaded in series to provide a 24 bit overall counting capability. When counter 44 has counted to the end-of-life number of strokes, the output of counter 44 goes high, which resets and holds counter 42. Counter 42 does not then thereafter further accumulate any additional stroke counts.

The output from counter 44 is applied to one input of NAND gate 46. The other input to NAND gate 46 is the output of buffer element 40. The output of NAND gate 46 is used to reset the timer logic circuit 48. As long as brushing continues (i.e. the brushhead is vibrating) the output of buffer element 40 will be low and timer logic circuit 48 thus will remain in a reset condition because the output of NAND gate 46 remains high.

When brushing terminates at the end of any one use, the output of buffer 40 will go high and if the output of counter 44 at that point is high, indicating that the end-of-life stroke number has been reached, the signal from NAND gate 46 to timer logic circuit 48 goes low, which allows timer logic circuit 48 to run. The output from NAND gate 46 is also applied to an inverting input of AND gate 50. Applied to the other input of AND gate so, which is also an inverting input, is a reset signal from pin 12 of timer logic circuit 48. When both inputs to AND gate 50 are low, a high output results which enables an oscillator 54 which in turn clocks the timer logic circuit 48.

In operation, each time that the lowest three bits (pins 1,2, and 3) of timer logic circuit 48 are high and the oscillator 54 signal is high, the resulting output of NAND gate 56, inverted by OR gate 58, pulses an LED drive circuit comprising resistor 60 and transistor 62. The output of the LED drive circuit is a low duty cycle pulse (approximately one per second in the embodiment shown, although this could be varied). LED 64 flashes in response to the drive signal.

After approximately two minutes the output pin 12 of timer logic circuit 48 goes high, which disables oscillator 54 via AND gate 50. The lowest 3 pins of circuit 48 are low at this point which results in a change of output of NAND gate 56, directing the LED drive circuit, preventing further flashes of the LED 64. Hence, in summary, after the end-of-life stroke number has been reached, LED 64 flashes once per second for 2 minutes after each brushing use and then stops, until the next brushing even occurs.

The circuit at this point draws only a very small current (less than 100 nanoamperes) which can be sustained by a small battery or capacitor.

During the detection of oscillations, the power created in the piezoelectric sensor 30 is greater than what is needed to power counters 42 and 44. This unneeded power could be used to charge the battery 36, if it is stored in a capacitor circuit, to maintain the counter memory between uses of the toothbrush, as well as powering the indicator circuit. Also, with a non-volatile memory and a capacitor, it is possible to power the circuit without a battery. The alarm indicator which signals that the end-of-life number of oscillations has occurred could also be a bistable device such as an LCD that changes opaqueness. Such a device would not require power to maintain it in an indicating condition.

Referring again to FIG. 1, as indicated briefly above, it should be understood that there are alternatives to the specific embodiment disclosed therein. For instance, while a piezoelectric transducer is used in the embodiment to produce information concerning the number of oscillations, other devices could be used, including a moving coil transducer or a Hall Effect magnetic sensor. In some cases, the signal information from the detection device may require conditioning of some sort so as to make it clearly recognizable. Such input regulation/conditioning circuits are well known. In many cases, however, such a conditioning circuit may not be necessary.

An alternative to the stroke counter 12 of FIG. 1 which counts up from zero to a specified end-of-life number, at which point the indicator timing circuit 18 is triggered, could be a count-down timer in which each of the signals from the detection device is used to count down from a predetermined end-of-life number. In this arrangement, the counter is non-volatile so that the count remains fixed between actual uses (brushing events). When the count down timer reaches zero, the indicator timing/alarm logic is triggered to produce the alarm. When a brushhead is replaced, the countdown timer is restored to the original end-of-life stroke number.

With respect to the alarm timing and the operation of the LED, the embodiment shown provides an alarm for a short period of time following each brushing event after the end-of-life stroke number has been detected. However, the timing circuit and the alarm can be arranged to provide alarm information which is periodic in a different fashion that disclosed or may be permanent, until the brushhead is replaced. The alarm itself may vary, including various visual devices as well as audible devices which have a particular tone or a rattling ball which is actuated by breaking/melting a connecting element when the end-of-life stroke number has been reached. It is also possible to use the piezoelectric transducer as the alarm element, i.e. the input device for counting the strokes also serves as the output device providing an alarm (audible). In the case of the piezoelectric transducer, the electrical signal from the timer logic is applied to the piezoelectric element to produce a sound.

It should also be understood that the present invention could be implemented mechanically, or with a combination of mechanical and electronic elements. One example of a mechanical stroke counter is a vibration type sensor involving a spring which is connected to the vibrating element (the brushhead arm). The spring has a mass on the other end thereof which results in a pawl-like element driving a gear. Another approach involves a spring loaded gear which is connected to and driven by the vibrating brushhead arm. Both gear arrangements could be used with a countdown type gear arrangement which is used to accumulate the total number of strokes.

In another mechanical arrangement, a horizontal strut is connected to the vibrating brushhead arm with the strut then connected to a pivoting lever arm, the free end of the lever arm driving a gear arrangement. A still further possibility involves an inflated bladder which is positioned so that it is in essence connected to the brushhead arm. The bladder senses the vibrations of the brushhead. A transducer is then used to produce a signal in response to the bladder action (e.g. a change in position or pressure in the bladder). Still other possibilities include a one way clutch and pin drive arrangement mounted on the brushhead arm which in turn drives a gear arrangement.

There are still other mechanical type arrangements which can be used to accumulate the number of actual brush strokes or oscillations.

With the correct gearing, the mechanical arrangement for a complete gearing cycle (corresponding to the end-of-life number of oscillations) can be used to move a dial or painted disk or activate a switch when the end-of-life number is reached. The dial or disk visual notification that replacement of the brushhead is due can be readily seen by the user. The switch can be used to complete a circuit with a battery for a visual or audible indication.

Certain of the mechanical arrangements discussed above, can also be used to trigger an electrical circuit which in turn provides an indication that the brushhead should be replaced. Accordingly, it should be understood that the implementation of the present invention can be accomplished in a number of different ways, both mechanically and electrically, or a combination thereof. The present invention is thus not limited to a specific structural embodiment. Further, it should be understood that while the present embodiment counts the number of strokes to obtain an indication of actual use of the toothbrush, other indicators of use which can be counted are also possible. One example is to count the actual number of brushing events, correlating the number to the six month period of use. Other use-based counting embodiments are also possible. Also, it should be understood that the system of the present invention could be part of an entire replaceable brushhead assembly.

Although a preferred embodiment of the present invention has been disclosed for purposes of illustration, it should be understood that various changes, modifications and substitutions may be incorporated in the embodiment within the spirit of the invention which is defined by the claims.

What is claimed is:

1. A system for determining when a brushhead portion of a power toothbrush should be replaced and for providing an indication thereof to a user, comprising:

a system carried within the toothbrush for detecting and accumulating the number of oscillations of the brushhead during operation of the toothbrush, wherein the detecting system includes a piezoelectric transducer which is actuated by the oscillations of the brushhead and detects said oscillations, and which is further adapted and arranged to generate power for a counter which forms part of the accumulating system, wherein the piezoelectric transducer in operation produces a signal output for each detected oscillation and applies the signal output to said counter;

means for determining when the number of said oscillations reaches a preselected number, said preselected number correlating to sufficient use of the brushhead that the brushhead should be replaced; and an indicator for communicating to the user that the brushhead should be replaced.

2. A system of claim 1, wherein the accumulating system includes a said counter which is responsive to a counted number of oscillations up to the preselected number and which produces an output signal when the preselected number is reached, and an assembly responsive to the output signal to drive the indicator.

3. A system of claim 2, wherein the indicator produces a visual indication.

4. A system of claim 2, wherein the indicator produces an audible indication.

5. A system of claim 1, wherein the counter in the accumulating system counts down to zero from the preselected number, the countdown counter producing an output signal when zero is reached, and an assembly responsive to the output signal to drive the indicator.

6. A system of claim 5, wherein the indicator produces a visual indication.

7. A system of claim 5, wherein the indicator produces an audible indication.

8. A system for determining when a brushhead portion of a power toothbrush should be replaced and for providing an indication thereof to a user, comprising:

a brushhead assembly which includes a brushhead;

a system carried within the brushhead assembly for detecting and accumulating the number of oscillations of the brushhead during operation of the toothbrush, wherein the system includes a piezoelectric transducer which is actuated by oscillations of the brushhead and detects said oscillations and which is adapted and arranged to generate power for a counter which forms part of the accumulating system, wherein the piezoelectric transducer in operation produces a signal output for each detected oscillation and applies the signal output to said counter;

means for determining when the number of said oscillations reaches a preselected number, said preselected number correlating to sufficient use of the brushhead that the brushhead assembly with the brushhead should be replaced; and an indicator for communicating to the user that the brushhead assembly should be replaced.

9. A system of claim 8, wherein said counter is responsive to a counted number of oscillations up to the preselected number and which produces an output signal when the preselected number is reached, and an assembly responsive to the output signal to drive the indicator.

10. A system of claim 9, wherein the indicator produces a visual indication.

11. A system of claim 9, wherein the indicator produces an audible indication.

12. A system of claim 8, wherein the counter counts down to zero from the preselected number, the countdown counter producing an output signal when zero is reached, and an assembly responsive to the output signal to drive the indicator.

13. A system of claim 12, wherein the indicator produces a visual indication.

14. A system of claim 12, wherein the indicator produces an audible indication.

* * * * *